US00PP28878P3

(12) United States Plant Patent
Stemkens

(10) Patent No.: US PP28,878 P3
(45) Date of Patent: Jan. 16, 2018

(54) ***AUBRIETA* PLANT NAMED 'ABRZ0004'**

(50) Latin Name: *Aubrieta hybrida*
Varietal Denomination: ABRZ0004

(71) Applicant: SYNGENTA PARTICIPATIONS AG, Basel (CH)

(72) Inventor: Henricus Godefridus Wilhelmus Stemkens, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 65 days.

(21) Appl. No.: 14/999,547

(22) Filed: May 23, 2016

(65) Prior Publication Data

US 2017/0135262 P1 May 11, 2017

Related U.S. Application Data

(60) Provisional application No. 62/252,740, filed on Nov. 9, 2015.

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Keith O Robinson
(74) *Attorney, Agent, or Firm* — Dale Skalla

(57) ABSTRACT

A new *Aubrieta* plant named 'ABRZ0004' particularly distinguished by its burgundy flowers, a compact and mounding habit with strong vigor, and a good winter hardiness.

1 Drawing Sheet

Latin name of the genus and species of the plant claimed: *Aubrieta hybrida.*

Varietal denomination: 'ABRZ0004'.

BACKGROUND OF THE NEW PLANT

The present invention comprises a new *Aubrieta*, botanically known as *Aubrieta hybrida* and hereinafter referred to by the variety name 'ABRZ0004'.

'ABRZ0004' is a product of a planned breeding program. The new cultivar 'ABRZ0004' has burgundy flowers, a compact and mounding habit with strong vigor, and is good winter hardy.

'ABRZ0004' originates from a hybridization in a controlled breeding program in a greenhouse in Enkhuizen, The Netherlands. The female parent was an unpatented, proprietary plant identified as 'L2011-1' with deep red flowers and less branching compared to 'ABRZ0004'.

The male parent of 'ABRZ0004' was an unpatented, proprietary plant identified as 'M1882-3' with a deep purple flower color, more branching, and later flowering compared to 'ABRZ0004'. The resultant seed was sown in August 2010 in a greenhouse in Enkhuizen, The Netherlands.

'ABRZ0004' was selected as one flowering plant within the progeny of the stated cross in March 2011 in a greenhouse in Enkhuizen, The Netherlands.

The first act of asexual reproduction of 'ABRZ0004' was accomplished when vegetative cuttings were propagated from the initial selection in June 2011 in a greenhouse in Enkhuizen, The Netherlands.

BRIEF SUMMARY OF INVENTION

Horticultural examination of plants grown from cuttings of the plant initiated in August 2011 in Enkhuizen, The Netherlands, and continuing thereafter, has demonstrated that the combination of characteristics as herein disclosed for 'ABRZ0004' are firmly fixed and are retained through successive generations of asexual reproduction.

'ABRZ0004' has not been observed under all possible environmental conditions. The phenotype may vary significantly with variations in environment such as temperature, light intensity, and day length.

A Plant Breeder's Right for this cultivar was applied for in the European Union on May 27, 2015 and assigned application number 2015/1068. 'ABRZ0004' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPH

The accompanying photographic drawing shows typical flower and foliage characteristics of 'ABRZ0004' with colors being as true as possible with an illustration of this type.

The photographic drawing shows in FIG. 1 a close-up of the flowers.

DETAILED BOTANICAL DESCRIPTION

The plant descriptions and measurements were taken in Enkhuizen, The Netherlands under natural light in March 2015. These plants were approximately 22 weeks old and were growing in 13 cm pots, in shade-house trials.

The plants used for the photographs were about 22 weeks old, grown in Enkhuizen, The Netherlands and taken in March 2015.

Color Chart used: Royal Horticultural Society Colour Chart (R.H.S.) 2001

TABLE 1

DIFFERENCES BETWEEN THE NEW VARIETY 'ABRZ0004' AND A SIMILAR VARIETY

| | 'ABRZ0004' | 'Axcent Lilac' (Not patented) |
|---|---|---|
| Plant shape: | Vigorous | Compact |
| Earliness: | 2 weeks earlier | Later |
| Flower color: | Deeper burgundy | More deep red |

Plant:

*Form, growth and habit.*—Mounding, spreading.
*Plant height.*—7 cm.
*Plant height (inflorescence included).*—11 cm.
*Plant width.*—18 cm.

Roots:

*Number of days to initiate roots.*—About 6 days at 18 degrees C.
*Number of days to produce a rooted cutting.*—2.5 weeks at 18 degrees C.
*Type.*—Fine, fibrous, free branching.
*Color.*—RHS N155B but whiter.

Foliage:

*Arrangement.*—Alternate.
*Immature, leaf color, upper surface.*—RHS 137A.
*Immature, leaf color, lower surface.*—RHS 138A.
*Mature, leaf color, upper surface.*—RHS 137A.
*Mature, leaf color, lower surface.*—RHS 138A-B.
*Length.*—2.5-3 cm.
*Width.*—1.5 cm.
*Shape.*—Oblanceolate.
*Base shape.*—Attenuate.
*Apex shape.*—Mucronulate.
*Margin.*—Medium dentation.
*Texture.*—Hirtellous.
*Color of veins, upper surface.*—RHS N144D.
*Color of veins, lower surface.*—RHS N144D.
*Pattern of veining.*—Pinnate.
*Petioles color.*—RHS N144D.
*Petioles length.*—0.5-1 cm.
*Diameter of petiole.*—0.5-0.6 cm.
*Texture.*—Pubescent.

Stem:

*Color of stem.*—RHS 147D.
*Length of stem.*—5-7 cm.
*Diameter.*—0.2 cm.
*Length of internodes.*—0.5 cm.
*Texture.*—Pilose.
*Color of peduncle.*—RHS 145B, at the base, to RHS 144B.
*Length of peduncle.*—2.5-3 cm.
*Peduncle diameter.*—0.2 cm.
*Texture.*—Pilose.
*Color of pedicel.*—RHS 144B to RHS 187A.
*Length of pedicel.*—1.2-1.5 cm.
*Diameter of pedicel.*—0.1 cm.
*Texture.*—Pubescent.

Inflorescence:

*Type: flowers.*—Single, cruciform, composed of 4 petals, flowers held above the plant.
*Number of flowers per inflorescence.*—7-15.
*Quantity of inflorescences per plant.*—About 38.
*Lastingness of individual blooms on the plant.*—15 days.
*Fragrance.*—Very light.

Bud (just before opening/showing color):

*Color of the sepals.*—RHS N186D, mostly at the base, mixed with RHS 143C.
*Length.*—1.2 cm.
*Width.*—0.5 cm.
*Shape.*—Oblong.

Corolla:

*Immature inflorescence.*—
*Diameter.*—2 cm.
*Color petals, upper surface.*—RHS N78A, very deep, more intense than when mature.
*Color petals, lower surface.*—RHS N79C.
*Mature inflorescence.*—
*Form.*—Rounded.
*Flower diameter.*—2.5-3 cm.
*Depth of flower.*—1.5 cm.
*Number of petals.*—4.
*Color petals, upper surface.*—RHS N78A, deep.
*Color petals, lower surface.*—RHS N78A.
*Length of petals.*—1.3-1.5 cm.
*Width of petals.*—1.8 cm.
*Petal shape.*—Spathulate.
*Shape characteristics.*—1 to 3 of the petals deeply divided all the way down the attachment.
*Apex shape.*—Rounded.
*Margin.*—Entire.
*Corolla texture, inside.*—Glabrous, papillose.
*Corolla texture, outside.*—Glabrous, papillose.
*Corolla tube color inside.*—RHS 154D+RHS 70B in the middle.
*Corolla tube, color outside.*—RHS N144D+RHS 70B in the middle.
*Duration of flowering.*—Continuous flowering throughout the Spring until end of May.

Calyx:

*Number of sepals.*—4.
*Color of sepals.*—RHS N79B.
*Length of sepals.*—1-1.1 cm.
*Width of sepals.*—0.3-0.5 cm.
*Sepal shape: 2 types.*—2 are oblanceolate situated on the opposite of each other, and 2 are oblong, also on the opposite of each other. The particularity is that the 2 oblong sepals are swollen at the base.
*Apex shape.*—For the oblanceolate shaped sepals: Obtuse. For the oblong ones: Acute.
*Margins.*—Entire.
*Texture, inner/upper surface.*—Smooth. Outer/lower surface: Stellate hairs.
*Base.*—Fused.

Reproductive organs:

*Gynoecium.*—
*Pistil quantity.*—1.
*Length.*—1 cm.
*Style color.*—RHS 145B with red just under the stigma RHS 171A.
*Style length.*—0.4 cm.
*Stigma color.*—RHS N145B.
*Stigma shape.*—Disc shaped.
*Ovary color.*—0.3-0.5 cm/RHS 144B.
*Androecium.*—
*Number of stamens.*—6.
*Length of stamens.*—0.8-1 cm.
*Anther color.*—2B.
*Anther length.*—0.1 cm.
*Anther shape.*—Ovate.

*Length filaments.*—0.6-0.8 cm.

*Color of filaments.*—RHS N155B to RHS 70B.

*Pollen amount.*—Moderate.

*Color of pollen.*—RHS 3B.

*Fertility/seed set.*—Neither seed nor fruit production has been observed.

*Disease/pest resistance.*—Resistance to pathogens and pests common to *Aubrieta* has not been observed.

*Drought tolerance and cold tolerance.*—Hardy perennial. Tolerates high temperature to at least 30 degrees C. Tolerates low temperatures to degrees minus 15 C. No specific drought tolerance has not been observed.

What is claimed is:

1. A new and distinct variety of *Aubrieta* plant named 'ABRZ0004' substantially as illustrated and described herein.

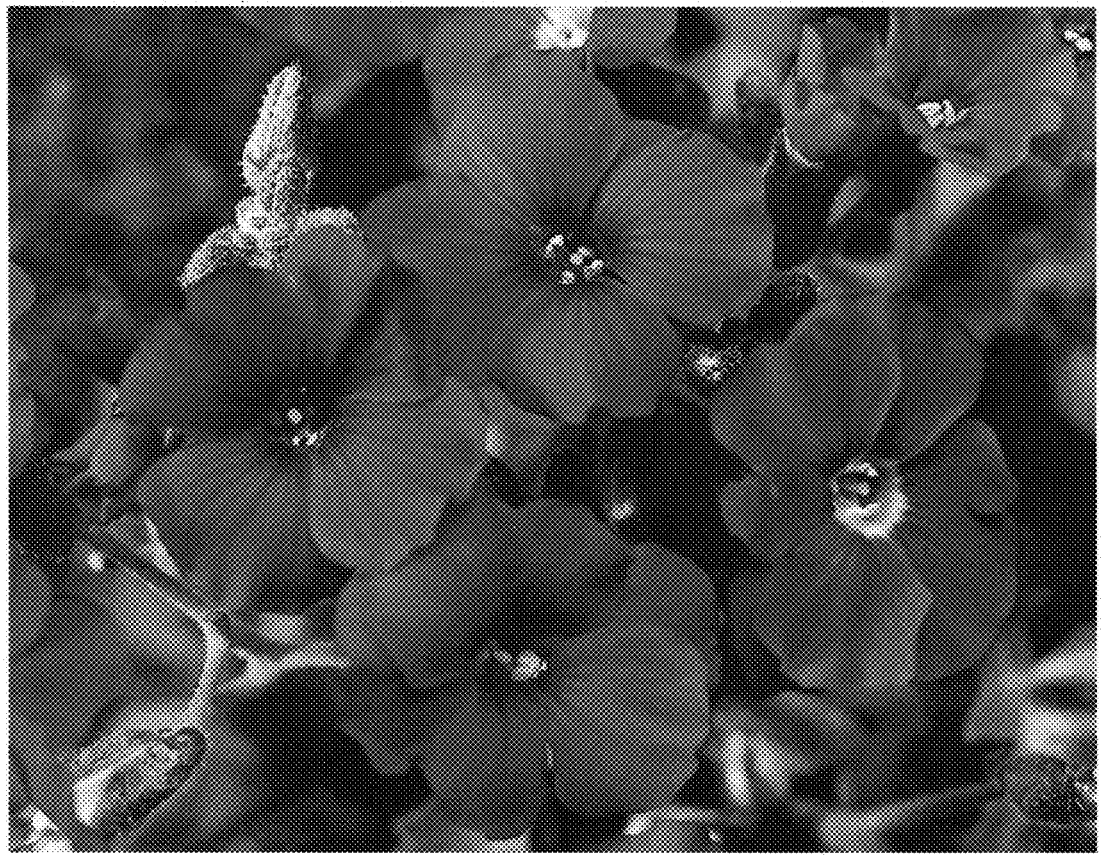

* * * * *